US00PP13436P2

(12) United States Plant Patent
Saul

(10) Patent No.: US PP13,436 P2
(45) Date of Patent: Dec. 31, 2002

(54) RUBUS PLANT NAMED 'GOLDEN QUILT'

(76) Inventor: Robert Mark Saul, 940 Carter Dr., Atlanta, GA (US) 30319

( * ) Notice: Subject to any disclaimer, the term of this patent is extended or adjusted under 35 U.S.C. 154(b) by 0 days.

(21) Appl. No.: 09/891,424

(22) Filed: Jun. 27, 2001

(51) Int. Cl.[7] ..... A01H 5/00
(52) U.S. Cl. ..... Plt./226

(58) Field of Search ..... Plt./226

*Primary Examiner*—Bruce R. Campell
*Assistant Examiner*—June Hwu
(74) *Attorney, Agent, or Firm*—C. A. Whealy

(57) ABSTRACT

A distinct cultivar of Rubus plant named 'Golden Quilt', characterized by its compact, prostrate and cascading plant habit; freely basal branching habit; yellow green-colored young foliage that turns green with development; and burgundy-colored foliage during the fall.

1 Drawing Sheet

BOTANICAL CLASSIFICATION/CULTIVAR DESIGNATION

*Rubus calycinoides* cultivar Golden Quilt.

BACKGROUND OF THE INVENTION

The present invention relates to a new and distinct cultivar of Rubus plant, botanically known as *Rubus calycinoides* and hereinafter referred to by the name 'Golden Quilt'.

The new Rubus is a naturally-occurring branch mutation of an unidentified selection of *Rubus calycinoides*, not patented. The new Rubus was discovered by the Inventor in a controlled environment in Atlanta, Ga. in May, 1998.

Asexual reproduction of the new Rubus by vegetative stem cuttings taken in a controlled environment in Dahlonega, Ga. since June, 1998, has shown that the unique features of this new Rubus are stable and reproduced true to type in successive generations.

SUMMARY OF THE INVENTION

The cultivar Golden Quilt has not been observed under all possible environmental conditions. The phenotype may vary somewhat with variations in environment such as temperature, daylength, light intensity, and water and nutritional status without, however, any variance in genotype.

The following traits have been repeatedly observed and are determined to be the unique characteristics of 'Golden Quilt'. These characteristics in combination distinguish 'Golden Quilt' as a new and distinct cultivar:

1. Compact, prostrate and cascading plant habit.

2. Freely basal branching habit.

3. Yellow green-colored young foliage that turns green with development.

4. Burgundy-colored foliage during the fall.

Plants of the new Rubus can be compared to plants of the parent, the unidentified Rubus selection. In side-by-side comparisons conducted in Atlanta, Ga., plants of the new Rubus and the unidentified Rubus selection differ in the following characteristics:

1. Plants of the new Rubus are slightly slower growing than plants of the unidentified Rubus selection.

2. Young leaves of plants of the new Rubus are yellow green in color whereas young leaves of plants of the unidentified Rubus selection are solid green in color.

BRIEF DESCRIPTION OF THE PHOTOGRAPH

The accompanying colored photograph illustrates the overall appearance of the new Rubus, showing the colors as true as it is reasonably possible to obtain in colored reproductions of this type. Colors in the photograph may differ slightly from the color values cited in the detailed botanical description which accurately describe the colors of the new Rubus.

The photograph comprises a top perspective view of a six month-old plant of 'Golden Quilt'.

DETAILED BOTANICAL DESCRIPTION

In the following description, color references are made to The Royal Horticultural Society Colour Chart except where general terms of ordinary dictionary significance are used. The following observations and measurements describe plants grown in Atlanta, Ga., under conditions which approximate commercial practice in an unshaded outdoor nursery. During the production of the plants, day temperatures ranged from 50 to 95° F. and night temperatures ranged from 30 to 80° F. Measurements and numerical values represent averages of six month-old plants grown in 15-cm containers. Measurements and color values were taken on plants during the spring and early summer.

Parentage: Naturally-occurring branch mutation of an unidentified selection of *Rubus calycinoides*, not patented.

Propagation:

*Type.*—By vegetative stem cuttings.

*Time to initiate roots.*—Summer: About 7 to 10 days at 85° F. Winter: About 10 to 14 days at 65° F.

*Time to produce a rooted cutting.*—Summer: About 28 days at 85° F. Winter: About 45 days at 65° F.

*Root description.*—Fine, freely branching, and white in color.

Plant description:

*Plant habit.*—Compact, prostrate, cascading.

*Growth habit.*—Freely basal branching; about 10 to 12 basal shoots per plant.

*Plant height.*—About 9 cm.

*Plant width.*—About 35 cm.

*Lateral branch description.*—Length: About 18 cm. Diameter: About 3 mm. Internode length: About 2.8 cm. Strength: Strong, flexible. Texture: Fine white pubescence; occasional random thorns on younger stems. Thorns about 1 mm in length, about 1 mm in height, and close to 183A to 187A in color. Color: Young stems: 144A to 144B. Mature stems: Close to 175A.

*Foliage description.*—Arrangement: Leaves simple; symmetrical; alternate. Length: From petiole attachment to apex: About 3.1 cm. From basal lobes to apex: About 4 cm. Width: About 4.2 cm. Shape: Roughly cordate with five rounded lobes. Apex: Rounded. Margin: Crenate. Texture: Upper surface: Waxy, smooth, sparsely pubescent. Lower surface: Densely pubescent. Aspect: Leaves face upright; concave. Venation pattern: Palmate. Color: Young foliage, upper surface: Initially mostly yellow green, between 7A and 154A; then venal areas, between 7A and 154A and interveinal areas, closest to 141A. Young foliage, lower surface: Closest to 147C to 147D, venation coloration similar to lamina. Mature foliage, upper surface: More green than 147A. Mature foliage, lower surface: Closest to 147C to 147D. Fall coloration, upper surface: Close to 185A. Fall coloration, lower surface: Closest to 147C to 147D. Venation, mature upper surface: Closest to 141A to 147A. Venation, mature lower surface: Closest to 145A.

*Petioles.*—Length: About 2.7 cm. Diameter: About 1 mm. Texture: Pubescent. Color: 144A to 144B.

*Stipules.*—Quantity/arrangement: Two at base of each petiole. Length: About 8 mm. Width: About 6 mm. Shape: Three-parted with acute apices. Texture: Upper surface: Smooth, glabrous. Lower surface: Pubescent. Color: Upper surface: Close to 143A. Lower surface: Close to 144A.

Flower description: Flower development has not been observed on plants of the new Rubus.

Disease resistance: Plants of the new Rubus have not been observed to be resistant to pathogens common to Rubus.

It is claimed:

1. A new and distinct cultivar of Rubus plant named 'Golden Quilt', as illustrated and described.

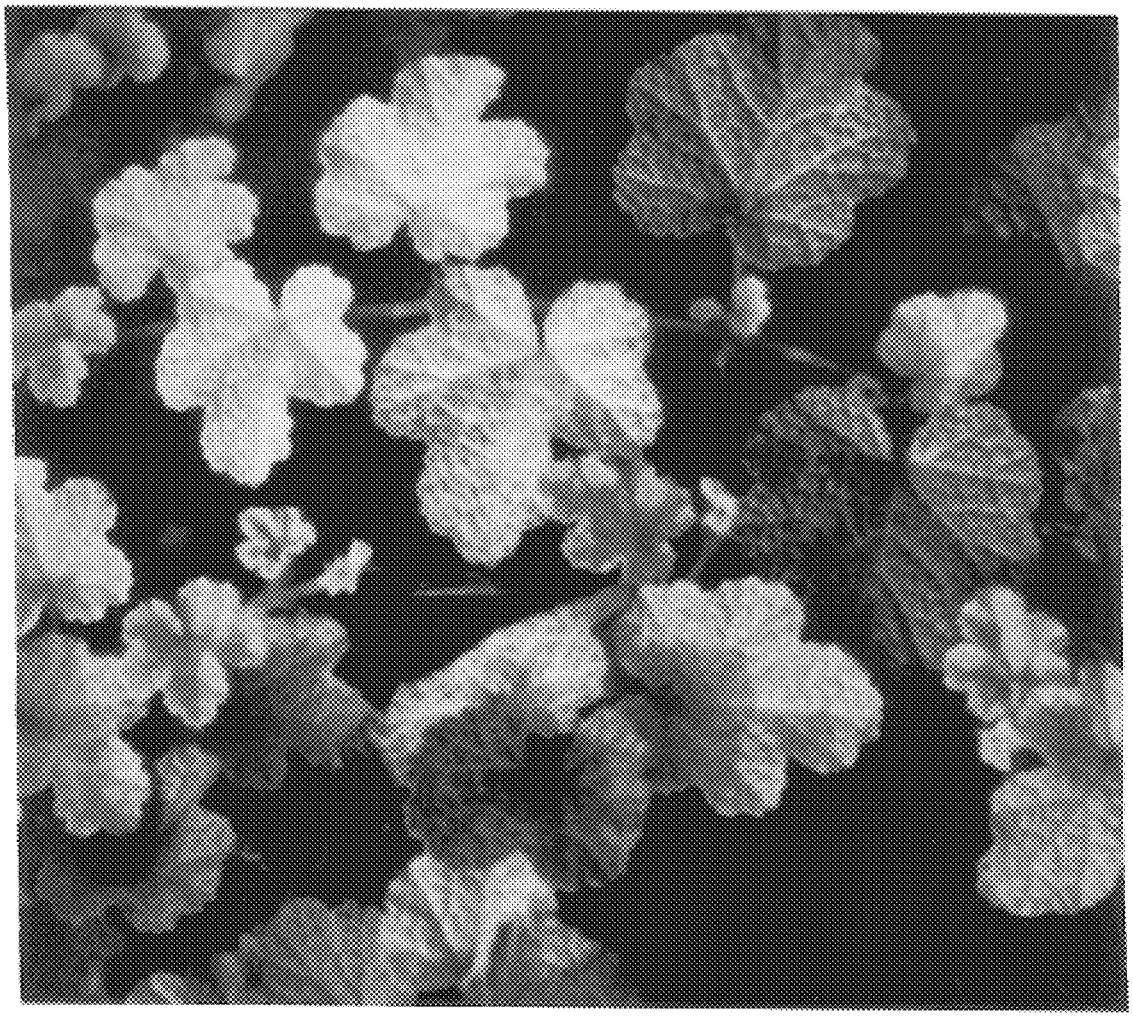

* * * * *